(12) United States Patent
Benna et al.

(10) Patent No.: US 9,012,866 B2
(45) Date of Patent: Apr. 21, 2015

(54) COMPACT PROTON THERAPY SYSTEM WITH ENERGY SELECTION ONBOARD A ROTATABLE GANTRY

(71) Applicant: Varian Medical Systems, Inc., Palo Alto, CA (US)

(72) Inventors: Manuel Benna, Bergisch Gladbach (DE); Michael Schillo, Bonn (DE); Jurgen Schultheiss, Cologne (DE); Luis Alberto Cruz, Miami, FL (US)

(73) Assignees: Varian Medical Systems, Inc., Palo Alto, CA (US); Varian Medical Systems Particle Therapy GmbH, Bergisch-Gladbach (DE)

( * ) Notice: Subject to any disclaimer, the term of this patent is extended or adjusted under 35 U.S.C. 154(b) by 0 days.

(21) Appl. No.: 14/033,950

(22) Filed: Sep. 23, 2013

(65) Prior Publication Data

US 2014/0275699 A1 Sep. 18, 2014

Related U.S. Application Data

(60) Provisional application No. 61/798,354, filed on Mar. 15, 2013.

(51) Int. Cl.
*G21K 5/04* (2006.01)
*A61N 5/10* (2006.01)

(52) U.S. Cl.
CPC ............................. *A61N 5/1077* (2013.01)

(58) Field of Classification Search
USPC ........... 250/396 R, 397, 398, 396 ML, 492.1, 250/492.3; 600/1; 315/500, 501, 502, 503, 315/504, 505
See application file for complete search history.

(56) References Cited

U.S. PATENT DOCUMENTS

| | | | |
|---|---|---|---|
| 4,870,287 A | 9/1989 | Cole et al. | |
| 6,683,318 B1 | 1/2004 | Haberer et al. | |
| 7,834,336 B2 | 11/2010 | Boeh et al. | |
| 8,053,746 B2 | 11/2011 | Timmer et al. | |
| 8,178,859 B2 | 5/2012 | Balakin | |
| 2012/0108958 A1* | 5/2012 | Jackson | 600/427 |
| 2012/0280150 A1 | 11/2012 | Jongen | |

FOREIGN PATENT DOCUMENTS

WO 2011036254 A1 3/2011

* cited by examiner

*Primary Examiner* — Nicole Ippolito (57) ABSTRACT

Systems and apparatuses for providing particle beams for radiation therapy with a compact design and suitable to a single treatment room. The radiation system comprises a stationary cyclotron coupled to a rotating gantry assembly through a beam line assembly. The system is equipped with a single set of dipole magnets that are installed on the rotating gantry assembly and undertakes the dual functions of beam energy selection and beam deflection. The energy degrader may be exposed to the air pressure. The beam line assembly comprises a rotating segment and a stationary segment that are separated from each other through an intermediate segment that is exposed to an ambient pressure.

25 Claims, 5 Drawing Sheets

COMPACT PROTON THERAPY SYSTEM WITH ENERGY SELECTION ONBOARD A ROTATABLE GANTRY

CROSS REFERENCE

The present application claims priority to U.S. Provisional Patent Application No. 61/798,354 filed on Mar. 15, 2013. The present disclosure is related to the U.S. patent titled "Irradiation device," U.S. Pat. No. 8,053,736, filed on Apr. 5, 2007, which claims priority to German patent application No. 202006019307.3, file don Dec. 21, 2006. The foregoing patent application and patent are hereby incorporated by reference in their entirety for all purposes.

TECHNICAL FIELD

Embodiments of the present disclosure relate generally to medical devices, and more particularly, to radiation therapy devices.

BACKGROUND

In a typical proton therapy system used for tumor radiation treatments for example, a proton beam is produced in a cyclotron or a synchrotron in a specific level of energy that can be adjusted to a prescribed energy level by virtue of energy selection then provided to a treatment station via a beam transportation system. Such a therapy system includes a particle accelerator, such as a cyclotron or a synchrotron, for providing the particle beam at a specific energy level. The beam transport system can tune and deliver the particle beam to a radiation station. At the end of the beam transport system, a rotational gantry associated with a radiation nozzle delivers the beam onto an irradiation object, e.g. a tumor of a patient, in a fixed position supported by the irradiation station during operation. Similar systems can be used for other heavy particle radiation treatment, such as neutron, He or C ion beam.

Typically a beam output from an accelerator has a fixed energy, e.g. 250 MeV. Depending on the diagnosis of a patient's condition, for example the depth of a tumor to be treated, different patients are prescribed with different depth doses of radiation. An energy selection system (ESS) is usually used to tune the fixed energy to the prescribed energy, e.g. 170 MeV. Conventionally, an ESS comprises an energy degrader for attenuating the beam energy roughly, followed by a set of energy selection dipole magnets dedicated for fine energy selection by filtering the undesired traverse emittances, momentum spread and energy spread resulted from the energy degrader. The transport system also includes a plurality of other magnets for beam focusing and steering purposes.

Figure 1:
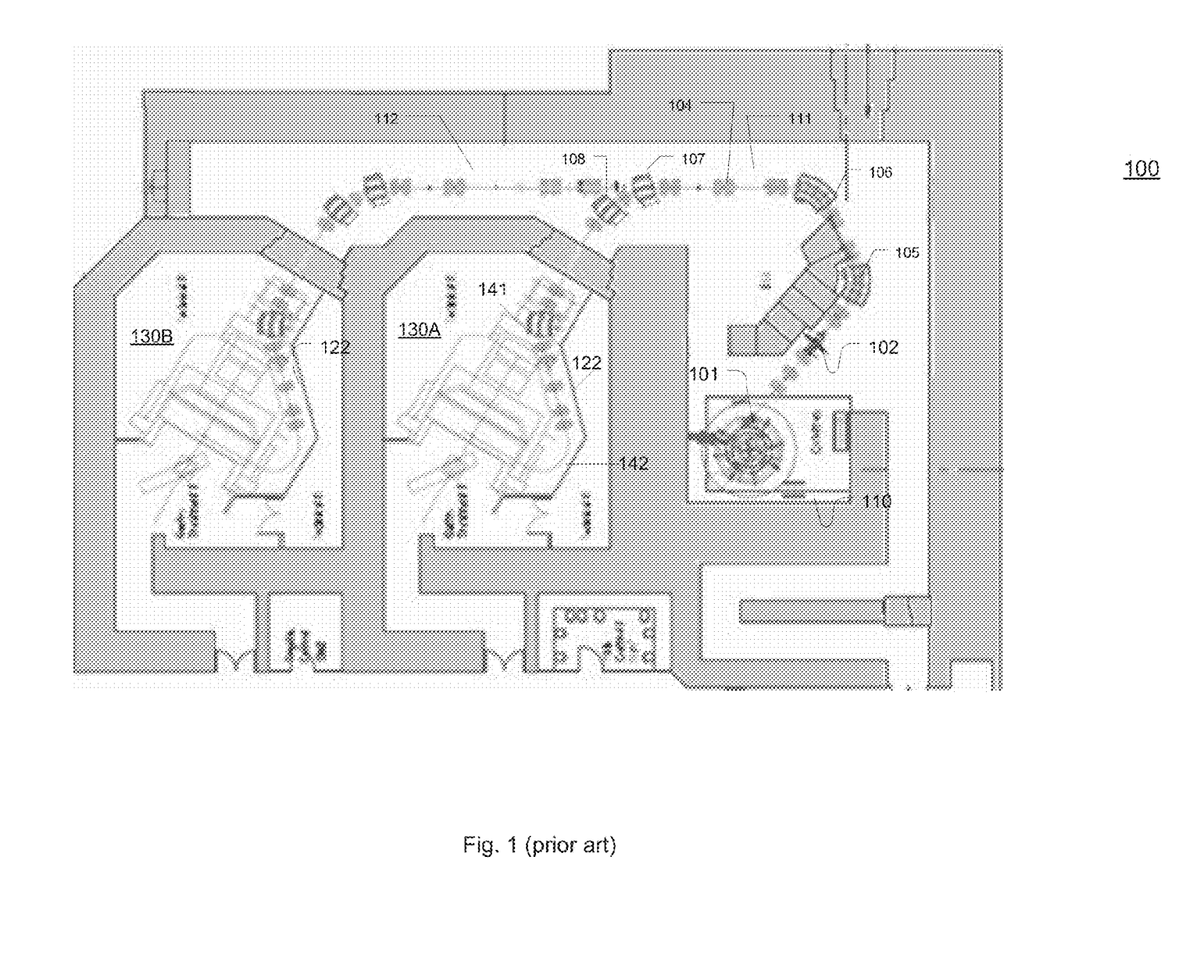
FIG. 1 illustrates a configuration of a medical facility that accommodates a proton radiation system providing proton beams for multiple treatment stations in accordance with the prior art.

Due to the high cost for purchasing and maintaining such a radiation system, a medical facility usually uses one accelerator for a plurality of treatment stations so the high expenditure for the accelerator facilities is distributed. FIG. 1 illustrates a configuration of a medical facility that accommodates a proton radiation system 100 providing proton beams for multiple treatment stations in accordance with the prior art. The system 100 comprises a single stationary cyclotron 101 located in a dedicated room 110, a carbon wedge energy degrader 102 disposed in a vacuum component of the beam line, a gantry 121 and 122 for each treatment room 131 and 132, and an ESS, several sets of quadrupole magnets for focusing the beam, e.g. 104, and a plurality sets of bending magnets that directs the proton beams from the cyclotron to respective treatment rooms, e.g. 131 and 132. As shown, the ESS of this system is composed of a carbon wedge degrader 102, and two dipole magnets 105 and 106 with an energy slit (not explicitly shown) sitting in between. The dipole magnets 105 and 106 are located proximate to the accelerator 101 and dedicated for selectively passing the particles with the targeted energy.

In order to supply the particle beams to different rooms located in various places relative to the accelerator room 110, the system 100 is equipped with long beam lines, e.g. 111 and 112, along different paths in which dipole magnets are used to change beam directions. For example, dipoles 107 and 108 are used to redirect the particle beam into the room 110. The dipole 141 bends the beam by 45° at the entrance of the gantry 121. Another dipole 142 bends the beam by 135° and toward the isocenter. Collectively, the two dipoles 141 and 142 in the gantry bends the beam by 90° from the beam line 111.

Although using a multi-station single-cyclotron system is effective to distribute the cost for large medical facilities, the overall cost for such a multi-gantry system may be prohibitively high for smaller facilities that may only need one treatment station. Also, some multi-station systems do not support simultaneous treatment in multiple stations. This contribute to further disadvantage that a delay at one treatment station can cause delay at the other station. Among the costly factors in the conventional proton radiation system, the dipole magnets consume significant expenditure associate with manufacture, installation, control, maintenance, and space that is limited and valuable in the medical facility.

Moreover, connecting to the stationary cyclotron and the rotating gantry, the beam line pipe comprises a rotating portion that can rotate along with the gantry and a stationary or non-rotating portion leading to the cyclotron, both portions being maintained under continuous low pressure (vacuum) typically in the 10E-05 mbar range. Conventionally, a rotating vacuum seal is used at the beam line connection between the stationary part of the beam line and the rotating part of the beam line to keep the pipe sealed from outside air during rotation.

SUMMARY OF THE INVENTION

Thus, it would be advantageous to provide a compact proton radiation system that has reduced cost and dimension and is feasible for single room proton therapy facility. Accordingly, embodiments of the present disclosure advantageously provide a radiation system that utilizes a set of dipole magnets on the gantry for the dual purposes of energy selection and redirecting the particle beam. By integrating the energy selection magnets onto the gantry, rather than in a dedicated section of the beam line, consumption of cost and space can be advantageously decreased, making the system suitable for a compact single-room design. Embodiments of the present disclosure further simplifies a proton radiation system by placing the energy degrader in the atmosphere and by replacing the vacuum seal with an air gap at the joint between the stationary portion and the rotating of the beam line.

In one embodiment of the present disclosure, a radiation therapy system for irradiating an irradiation object with particle beam in a predetermined energy comprises a stationary particle accelerator, a beam line assembly, an energy degrader, and a swiveling gantry assembly. The beam line assembly is operable to direct and focalize a particle beam along a first direction. The energy degrader is operable to attenuate the energy of the particle beam and may be exposed to an air pressure. The swiveling gantry assembly comprises a set of dipole magnets as well as additional quadrupole and steerer magnets, all with controllable magnetic fields, and a collimator disposed in between the dipole magnets. The set of dipole magnets are operable to select a portion of the particle beam with a predetermined energy, and redirect the portion of the beam to a second direction. The set of dipole magnets may comprise a 45° and a 135° magnet arranged in sequence. The swiveling gantry may be capable of rotating 360° about the first direction and may comprise a housing that has a first member made of low-Z material and a second member made of high-Z material. The beam line assembly may comprise a rotating segment and a stationary segment couple to respective vacuum apparatuses. The rotating segment and the stationary segment may be separated by an air gap.

The foregoing is a summary and thus contains, by necessity, simplifications, generalizations and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

Embodiments of the present invention will be better understood from a reading of the following detailed description, taken in conjunction with the accompanying drawing figures in which like reference characters designate like elements and in which.

DETAILED DESCRIPTION

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail so as not to unnecessarily obscure aspects of the embodiments of the present invention. Although a method may be depicted as a sequence of numbered steps for clarity, the numbering does not necessarily dictate the order of the steps. It should be understood that some of the steps may be skipped, performed in parallel, or performed without the requirement of maintaining a strict order of sequence. The drawings showing embodiments of the invention are semi-diagrammatic and not to scale and, particularly, some of the dimensions are for the clarity of presentation and are shown exaggerated in the drawing Figures. Similarly, although the views in the drawings for the ease of description generally show similar orientations, this depiction in the Figures is arbitrary for the most part. Generally, the invention can be operated in any orientation.

NOTATION AND NOMENCLATURE

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "processing" or "accessing" or "executing" or "storing" or "rendering" or the like, refer to the action and processes of a computer system, or similar electronic computing device, that manipulates and transforms data represented as physical (electronic) quantities within the computer system's registers and memories and other computer readable media into other data similarly represented as physical quantities within the computer system memories or registers or other such information storage, transmission or display devices. When a component appears in several embodiments, the use of the same reference numeral signifies that the component is the same component as illustrated in the original embodiment.

DESCRIPTION OF THE INVENTION

Figure 2:
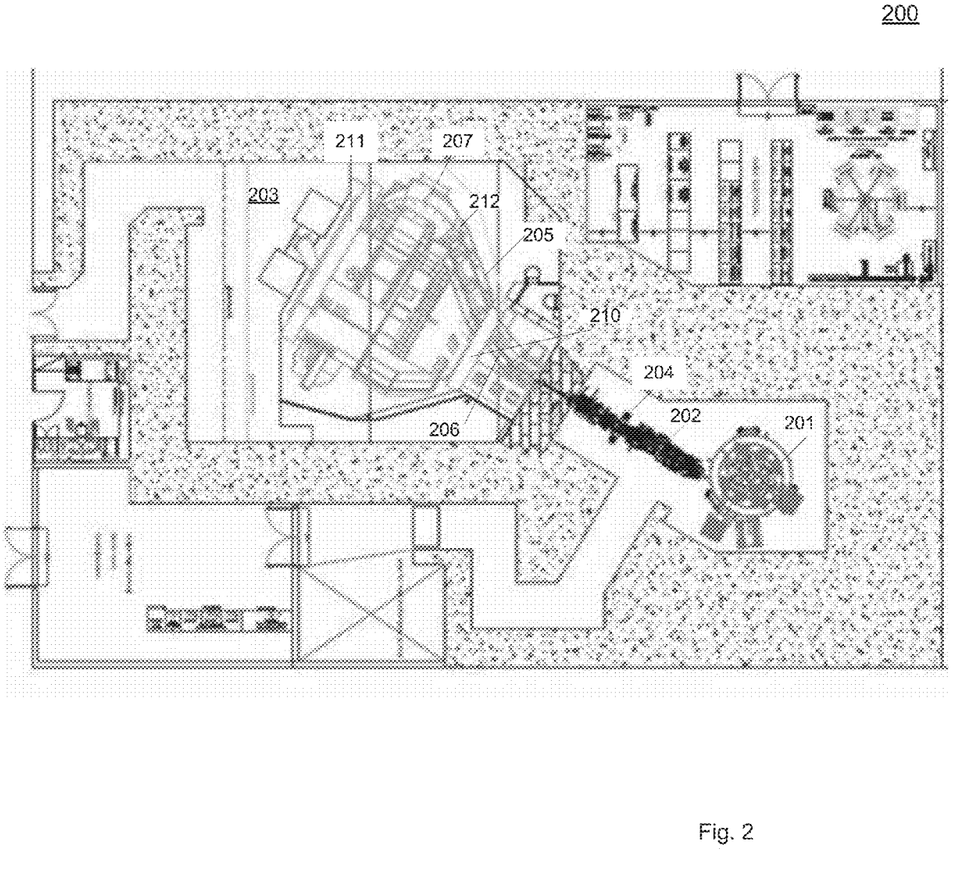
FIG. 2 is an exemplary configuration of a medical facility equipped with a single-room proton therapy system in accordance with an embodiment of the present disclosure.

FIG. 2 is an exemplary configuration of a medical facility equipped with a single-room proton therapy system 200 in accordance with an embodiment of the present disclosure. The compact radiation system 200 is designed to deliver a proton beam from the stationary cyclotron 201 to an adjacent single treatment room 203. The proton radiation system 200 includes an accelerator 201, e.g. a cyclotron as shown, a short beam line 202 transporting the particle beam from the cyclotron 201 to the single treatment room 203 along a linear axis, an energy degrader 204 disposed in the beam line 202, a single set of dipole magnets 206 and 207, and a swiveling gantry 205 operable to deliver a proton beam to the treatment station through a nozzle in different angles. In the single-room configuration 200, the cyclotron can be placed near the treat room as close as practically possible, and thus the beam line 204 can be short and linear, reducing the need for dipole magnets used for reorienting a particle beam. The system may further comprise a plurality of sets of focusing magnets mounted in the beam path to focus the particle team.

In contrast to the multi-station system in FIG. 1, the single-room system 200 has a simplified arrangement of dipole magnets as well as the entire transporting system. Particularly, the dipole magnets 206 and 207 installed on the gantry 205 undertake the dual functions of energy selection as well as deflecting the particle beam from the beam line axis to the isocenter of the treatment station. In the illustrated embodiment, the 45° dipole magnet 206 located at the entry point of the gantry and the 135° dipole magnet 207 downstream can collectively bend the particle beam by 90° from the beam line 202 axis. At the same time, when the current in the coils of the magnets 206 and 207 is controlled to a precise current according to a target energy level, the magnets 206 and 207 in combination with a beam collimator are operable to perform the energy selection function.

By integrating the ESS magnets in the gantry assembly, rather than in a dedicated section of the beam line as in the prior art, system consumption of cost and space can be advantageously and remarkably reduced, making the system suitable for a single-room design and more accessible to relatively small clinics. A beam optics simulation on the beam profile along the beam path proves that the simplified magnet system as illustrated in FIG. 2 is feasible to provide substantially identical clinical specification, such as beam size and shape for example, as resulted from a corresponding conventional multi-room radiation system that has separate dedicated ESS magnets and the deflection magnets.

The disclosure is not limited by the angles, configurations or locations of the dual-function magnets. For instance, the magnets may comprise three 90° magnets that can collectively bend the beam by 90°. However, using the minimum number (two) of dipole magnets to reorient the magnets furthers the purposes of cost-efficiency and compact design. A set of scanning magnets can be used to control the raster scan of the particle beam. In some embodiment, the scanning magnets 211 can be placed in between the set of dual-function magnets 206 and 207. In the illustrated embodiment, the scanning magnets can be placed downstream after the magnet 207 and near the nozzle, which contributes to yet another design for a smaller gantry.

The magnetic fields generated by the deflection/energy selection magnets 206 and 207 can be controlled by software programs to guide the beam as well as select the beam of desire energy. The software program can be implemented by any known computer implemented methods. In some other embodiment, the deflection magnets may comprise two 45° dipole magnets and collectively bend the beam by 90°. In some other embodiments, the deflection magnets may collectively bend the beam by 135° or any other angle. Any other suitable configuration of the deflection magnets can be used to practice the present disclosure. The deflection/energy selection magnets can be controlled by software programs to achieve a specific particle energy dictated by each specific treatment plan.

The present disclosure can be implemented with any type of collimator suitable for particle beam energy selection that is disposed downstream after an energy selection magnet. The collimator 212 may comprise energy slits, apertures, and/or orifices disposed in between the two magnets 206 and 207. In some embodiments, the positions and openings of the collimators may be controllable. In some embodiments, the collimator features a compact design, such as an energy selection slit in a slim form, which can advantageously contribute to further reduction in system consumption of cost and space.

Still in some other embodiments, the energy selection function can be solely assumed by a combination of suitable magnetic components and one or more energy degraders, which may advantageously eliminate the need for a collimator in an energy selection system. For example, a set of additional magnets may be used to narrow the spatial cross section and/or energy spectrum of the beam that exits from an energy degrader.

In the illustrated embodiment, the energy degrader 204 comprises a carbon wedge disposed under a vacuum chamber situated in the beam line 202 and proximate to the accelerator 201. Any other suitable energy degrader can be used to implement the present disclosure. In some other embodiments, the energy degrader material can be integrated in the gantry as well, and disposed proximate to the deflection/energy selection magnets. In still some other embodiments, the degrader may be exposed to ambient pressure, which can advantageously save cost related to material, manufacturing and installation etc. Still in some other embodiments, the degrader, in conjunction with other magnet fields on the system, may be configured such that the beam at its exit point has a narrow spatial cross section and energy spectrum, eliminating the need for a collimator.

The gantry assembly 205 may be rotatable while the accelerator remains stationary. The system may be equipped with a swiveling device that renders the rotations of the gantry such that the particle beam can impinges on the isocentrically arranged irradiation station in various directions. In some embodiments, the gantry can swivel 360° about an axis that is substantially parallel to the beam line axis such that the particle beam can impinge on an isocenter in a full circle.

The gantry is coupled to a nozzle operable to emit the particle beam onto the radiation object. The nozzle may be coupled to a set of deflection magnets 211 that deflect the beam in mutually orthogonal directions for purposes of traverse scan, e.g. X-Y scan. The nozzle may be coupled to means for monitoring beam position and means for monitoring the radiation dose. The nozzle and the focusing magnets may also be integrated in the gantry. In some embodiments, the nozzle is rotatable and capable of raster scan in two or three dimensions.

In some embodiments, the nozzle is capable of pencil-beam scan where the particle beam can be focused on a beam cross-section which lies distinctly below the size of typical irradiation volumes. The peak deposition of the radiation dose along the radiation path corresponds to the Bragg peak location determined by the particle energy. By using a suitable focused pencil beam, many small volumes, so-called voxels, thus can be irradiated, so that the irradiation volumes of any shape, conformal to the specific shape of a tumor, can be raster-scanned. The depth scan can be achieved by varying the particle energy, for example through the ESS.

The gantry may comprise a shielding plug 210 which reduces neutron dose risk near the patient. There may be additional shielding around the beam line. The shielding plug may be a cylindrical sphere or any other suitable configurations. The gantry may comprise hybrid materials to balance the cost reduction and protection against undesirable neutron dose risk. In some embodiments, high-Z material shields, such as lead (Pb), are used at places along gantry that would be prevalent to radiation/neutron emission. Cheaper/lighter materials, such as C, can be used in any other places, for example, the part of the gantry that does not face the patient.

The present disclosure is not limited to any particular type of accelerator or the associated particle source. In some embodiments, the accelerator may be a cyclotron, for example a superconducting synchrocyclotron in a compact design. In some embodiments, the accelerator may be able to provide protons, neutron, electrons, or heavy ion, such as He2+ or C6+ particles.

Figure 3:
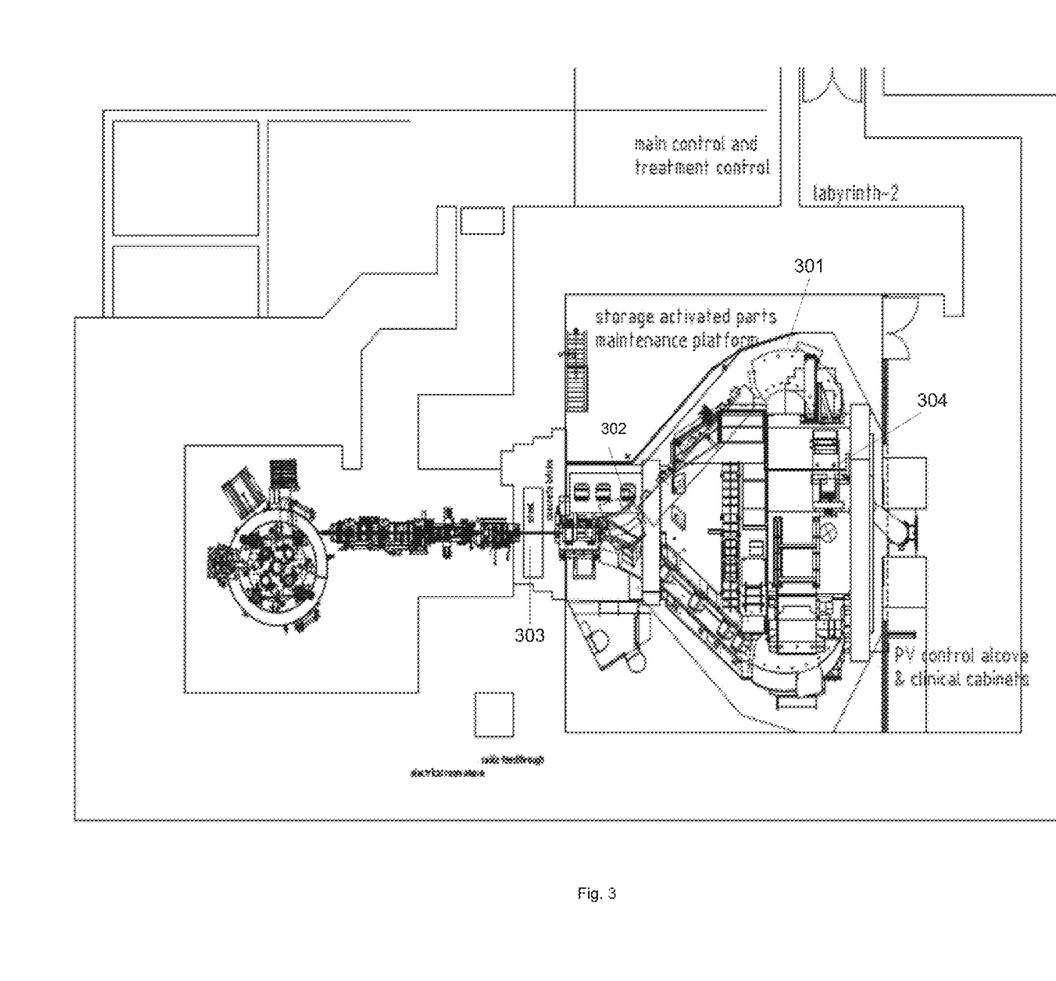
FIG. 3 is a side view diagram illustrates the mechanical schematics of the compact radiation system equipped with a set of deflection/energy selection magnets and in accordance with an embodiment of present disclosure.

FIG. 3 is a side view diagram illustrates the mechanical schematics of the compact radiation system equipped with a set of deflection/energy selection magnets 301 and 302 in accordance with an embodiment of present disclosure.

In some embodiments of a single-room radiation system in accordance with the present disclosure, the entire beam line, including the rotating portion leading to the gantry and the non-rotating portion leading to the accelerator, is under vacuum. The rotating portion and the non-rotating portion are connected through a vacuum seal. In the illustrated embodiment, the beam is transferred from stationary to rotating parts via a small air gap 303 and two thin kapton (polymide film) windows for example. Thus, each portion has its own vacuum devices and independent of the other portion. This advantageously further simplifies the system, by eliminating the need for a rotating, mechanical vacuum joint, and reduces material cost, simplifies maintenance and less vacuum leaks on the beam pipe.

Besides the components described with reference to FIG. 2, FIG. 3 also illustrates the other pertaining components, including storage activated parts and a PV control alcove, and can be appreciated by those with ordinary skills in the art.

Figure 4:
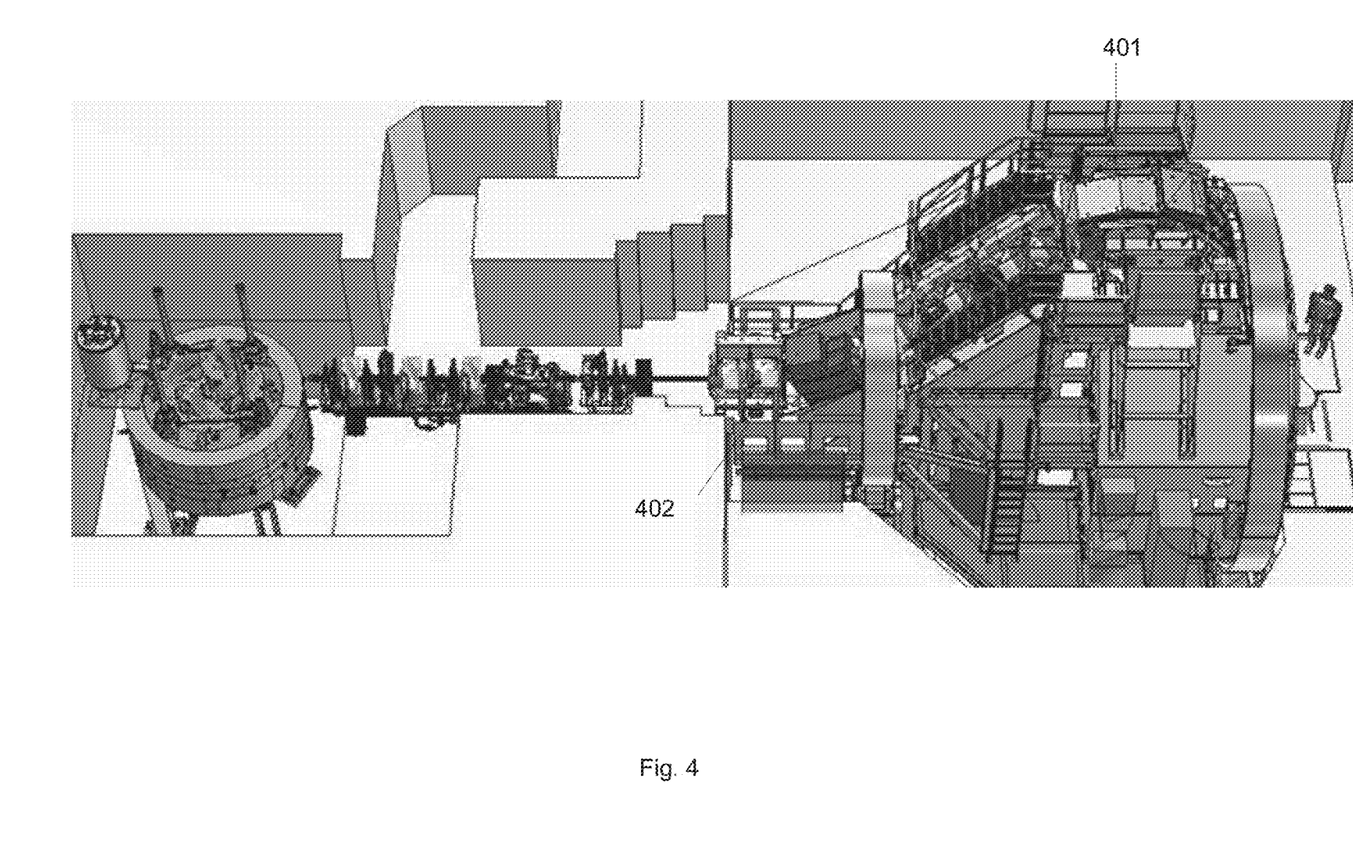
FIG. 4 is a 3D view diagram illustrating the exterior mechanical schematics of the compact radiation system equipped with a set of deflection/energy selection magnets and in accordance with an embodiment of present disclosure.

FIG. 4 is a 3D view diagram illustrating the exterior mechanical schematics of the compact radiation system equipped with a set of deflection/energy selection magnets 401 and 402 in accordance with an embodiment of present disclosure.

Figures 5A, 5B:
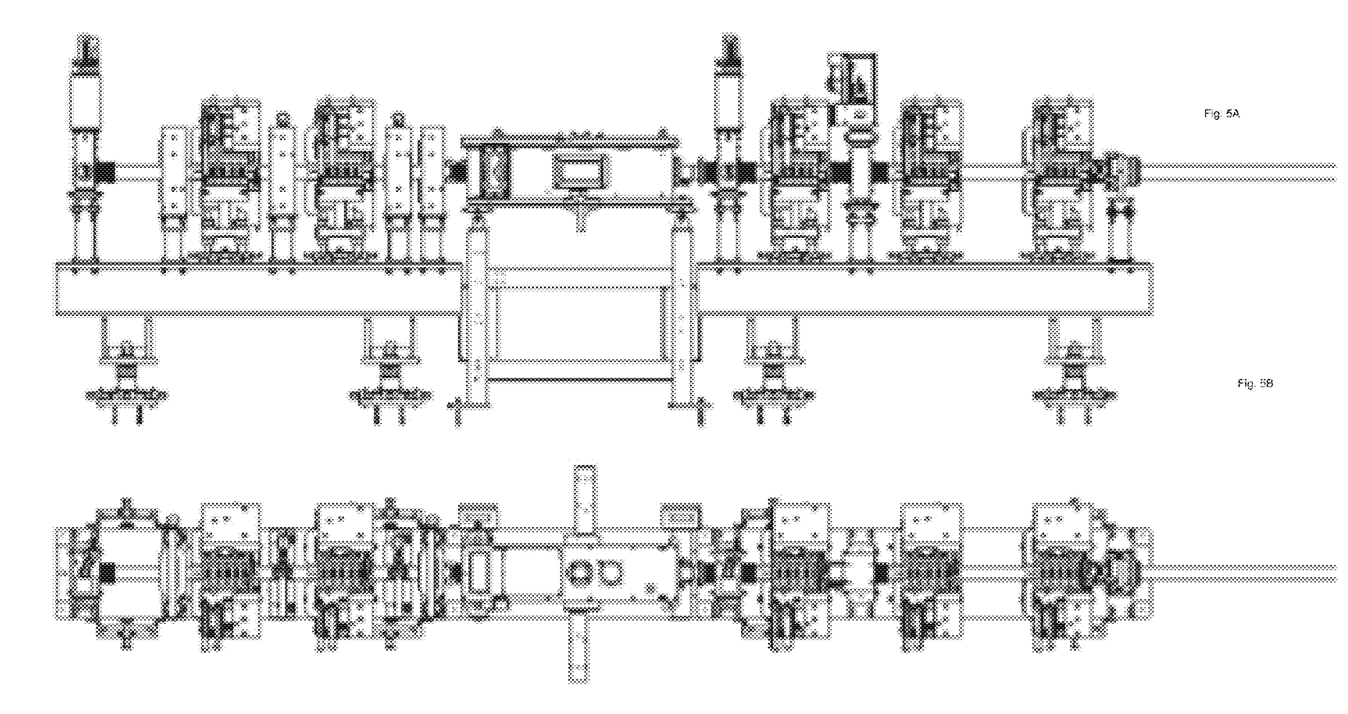
FIG. 5A illustrate a side view of the beam line in that transport the particle beam from the cyclotron to the gantry in accordance with an embodiment of the present disclosure.
FIG. 5B illustrate a top view of the beam line in that transport the particle beam from the cyclotron to the gantry in accordance with an embodiment of the present disclosure.

FIG. 5A and FIG. 5B illustrate a side view and a top view of the beam line in that transport the particle beam from the cyclotron to the gantry in accordance with an embodiment of the present disclosure.

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A radiation therapy system for irradiating an irradiation object with particle beams of a predetermined energy, said radiation therapy system comprising:
   a stationary particle accelerator configured to provide a particle beam;
   a beam line assembly coupled to said stationary particle accelerator and operable to direct said particle beam along a first direction;
   an energy degrader operable to attenuate an energy of said particle beam; and
   a swiveling gantry assembly coupled to said beam line assembly and comprising:
      a set of dipole magnets with controllable magnetic fields; and
      a collimator disposed in between said set of dipole magnets,
   wherein said set of dipole magnets in combination with said collimator; are operable to select a portion of said particle beam with said predetermined energy for irradiating said irradiation object, and to redirect said portion of said particle beam to a second direction.

2. The radiation therapy system of claim 1, wherein said swiveling gantry assembly is operable to swivel substantially 360° about said first direction, and wherein said beam line assembly comprises quadrupole magnets and steering magnets, beam monitors.

3. The radiation therapy system of claim 1, wherein further said energy degrader comprises a carbon wedge degrader disposed within said beam line assembly and exposed to an atmosphere pressure.

4. The radiation therapy system of claim 1, wherein said stationary particle accelerator comprises a superconducting cyclotron and is operable to provide said particle beam with 250 MeV.

5. The radiation therapy system of claim 1, wherein said particle beam comprises particles selected from a group consisting of protons, neutron, He ions, and C ions.

6. The radiation therapy system of claim 1, wherein said set of dipole magnets are operable to collectively redirect said portion of said particle beam by 90° substantially.

7. The radiation therapy system of claim 1, wherein said swiveling gantry assembly further comprises a nozzle operable to guide and control emission of said portion of said particle beam toward an isocenter, wherein further said nozzle is configured to scan in three dimensions.

8. The radiation therapy system of claim 6, wherein said set of dipole magnets comprise a 45° and a 135° dipole magnets arranged in sequence, and wherein further said beam line assembly comprises no dipole magnets.

9. The radiation therapy system of claim 1, wherein said swiveling gantry assembly comprises an exterior housing comprising a first member made of high-Z material and a second member made of low-Z material.

10. The radiation therapy system of claim 1, wherein said beam line assembly comprises a rotating segment and a stationary segment, each segment coupled with a respective vacuum apparatus, and wherein said rotating segment is separated from said stationary segment by an intermediate segment that is exposed to an ambient pressure.

11. A heavy particle radiation therapy system suitable for providing radiation particle beams for a single treatment station comprising:
   a particle accelerator configured to provide a particle beam;
   a beam line assembly coupled to said particle accelerator and operable to directing said particle beam to a swiveling gantry assembly;
   an energy degrader operable to attenuate an energy of said particle beam and exposed to an ambient pressure; and
   said swiveling gantry assembly coupled to said beam line assembly and comprising:
      a set of dipole magnets with controllable magnetic field; and
      a beam collimator, wherein said set of dipole magnets in combination with said beam collimator are configured to select a portion of said particle beam with a predetermined energy, and to redirect said portion of said particle beam to a second direction.

12. The heavy particle radiation therapy system of claim 11, wherein said set of dipole magnets are operable to collectively bend said portion of said particle beam by 90° substantially.

13. The heavy particle radiation therapy system of claim 11, wherein said beam line assembly comprises no dipole magnet.

14. The heavy particle radiation therapy system of claim 11, wherein said beam collimator comprises an energy selection slit and is situated between said set of dipole magnets.

15. The heavy particle radiation therapy system of claim 11, wherein said particle accelerator remains stationary during operation.

16. A heavy particle radiation therapy system of claim 11, wherein said energy degrader is disposed within said swiveling gantry assembly.

17. A proton radiation therapy system configured to provide proton beam radiation to a single treatment station, said proton radiation therapy system comprises:
   a cyclotron coupled to a proton source;
   a beam line assembly coupled to said cyclotron and operable to direct said particle beam to a swiveling gantry assembly;

an energy degrader operable to attenuate an energy of a proton beam;

said swiveling gantry assembly coupled to said beam line assembly and comprising:
 a set of dipole magnets; and
 a beam collimator, wherein said set of dipole magnets in combination with said beam collimator are operable to select a portion of said proton beam with a predetermined energy for irradiating an irradiation object, and collectively to redirect said portion of said particle beam by substantially 90°.

18. The proton radiation therapy system of claim 17, wherein said beam line assembly extends in a linear axis, and wherein said swiveling gantry assembly is operable to swivel 360° about said linear axis.

19. The proton radiation therapy system of claim 17, wherein said energy degrader is exposed to an ambient pressure.

20. The proton radiation therapy system of claim 17, wherein said set of dipole magnets comprise a 45° and a 135° dipole magnets arranged in sequence, wherein said beam line assembly comprises no dipole magnets, and wherein further said beam line assembly comprises a rotating segment and a stationary segment, wherein said rotation segment and said stationary segment are coupled to respective vacuum systems, and wherein said rotating segment is separated from said stationary segment by an intermediate segment that is exposed to an ambient pressure.

21. A radiation therapy system for irradiating an irradiation object with particle beams of a predetermined energy, said radiation therapy system comprising:
 a stationary particle accelerator configured to provide a particle beam;
 a beam line assembly coupled to said stationary particle accelerator and operable to direct said particle beam along a first direction;
 an energy degrader operable to attenuate an energy of said particle beam; and
 a swiveling gantry assembly coupled to said beam line assembly and comprising multiple sets of dipole magnets with controllable magnetic fields,
 wherein said multiple set of dipole magnets are operable to select a portion of said particle beam with said predetermined energy for irradiating said irradiation object, and to redirect said portion of said particle beam to a second direction.

22. The radiation therapy system of claim 21, wherein said swiveling gantry assembly comprises no collimator used for energy selection.

23. The radiation therapy system of claim 21, wherein beam line assembly has varying beamline widths configured for energy selection.

24. The radiation therapy system of claim 21, wherein said swiveling gantry assembly comprises an exterior housing comprising a first member made of high-Z material and a second member made of low-Z material.

25. The radiation therapy system of claim 21, wherein said beam line assembly comprises a rotating segment and a stationary segment, each segment coupled with a respective vacuum apparatus, and wherein said rotating segment is separated from said stationary segment by an intermediate segment that is exposed to an ambient pressure.

* * * * *